Figure 5:
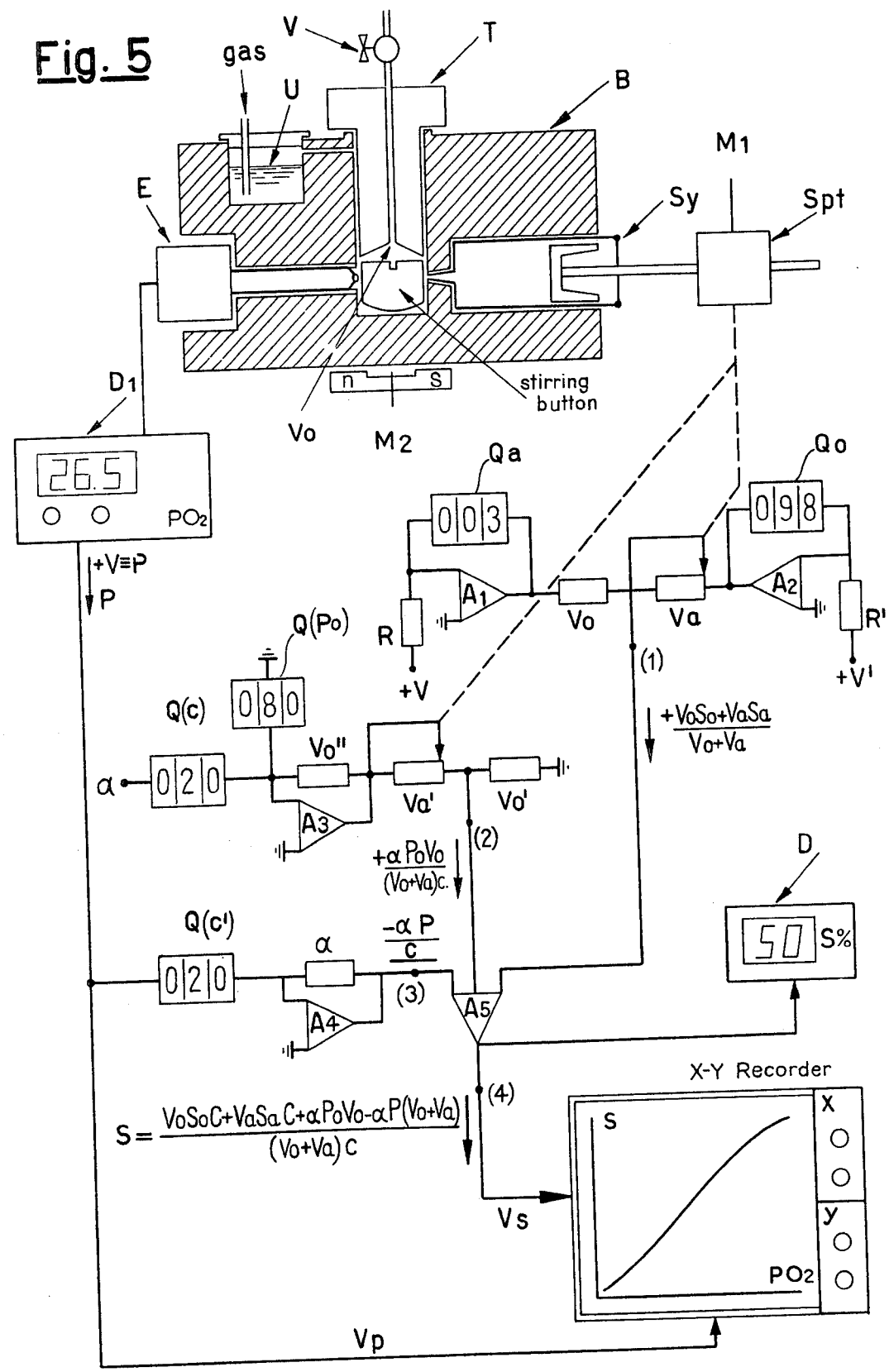

United States Patent [19]

Raffaele

[11] 4,097,921
[45] Jun. 27, 1978

[54] METHOD AND APPARATUS FOR AUTOMATICALLY DETERMINING THE DILUTION CURVE OF A SOLUTION, PARTICULARLY THE OXYGEN DISSOCIATION CURVE OF BLOOD OR HEMOGLOBIN SOLUTIONS

[75] Inventor: Italo Raffaele, Milan, Italy

[73] Assignee: Luigi Rossi, Milan, Italy

[21] Appl. No.: 744,825

[22] Filed: Nov. 24, 1976

Related U.S. Application Data

[63] Continuation-in-part of Ser. No. 598,163, Jul. 22, 1975, abandoned.

[30] Foreign Application Priority Data

Jul. 26, 1975  Italy ................................ 25627 A/75

[51] Int. Cl.² ............................................ G01N 33/16
[52] U.S. Cl. .................................. 364/416; 23/230 R
[58] Field of Search ...................... 235/151.35, 151.12; 23/230 B, 230 R, 254 E; 364/416

[56] References Cited

U.S. PATENT DOCUMENTS

| | | | |
|---|---|---|---|
| 3,775,595 | 11/1973 | Rosse et al. | 235/151.35 X |
| 3,849,070 | 11/1974 | Garza et al. | 23/230 R |
| 3,864,084 | 2/1975 | Folkman | 23/230 R |
| 3,879,604 | 4/1975 | Malmvig | 235/151.12 X |
| 3,895,630 | 7/1975 | Bachman | 23/254 E X |

*Primary Examiner*—Edward J. Wise
*Attorney, Agent, or Firm*—Cushman, Darby & Cushman

[57] ABSTRACT

The invention relates to an apparatus for automatically determining the oxygen dissociation curve (ODC) of whole blood or of a hemoglobin solution. Blood or hemoglobin having a predetermined oxygen saturation level are admixed with deoxygenated blood or a hemoglobin solution and the oxygen partial pressure of the mixture, while being formed, is measured. The output of the $P_{O_2}$ electrode, in the form of an electrical signal, is fed into a computer and two functions of the $P_{O_2}$ (saturation and total oxygen) are calculated, giving the required curve by means of recording and/or displaying means. In this way, the ODC can be determined for whole blood under near physiological conditions of pH, hemoglobin concentration, hematocrit, temperature, $P_{CO_2}$, and organic phosphates content.

9 Claims, 9 Drawing Figures

Fig. 1A
Fig. 1B
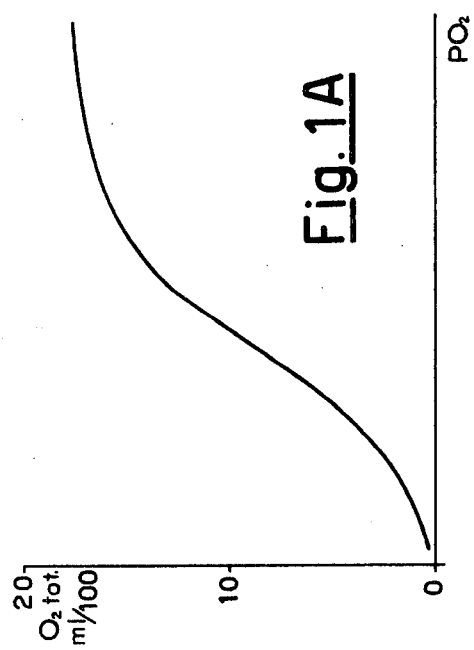
Fig. 2

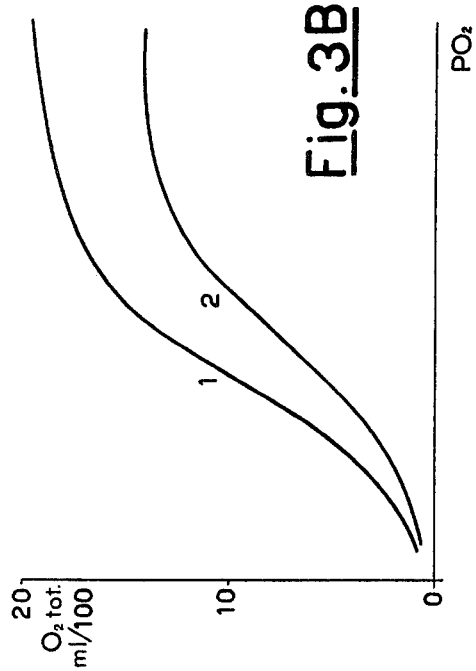
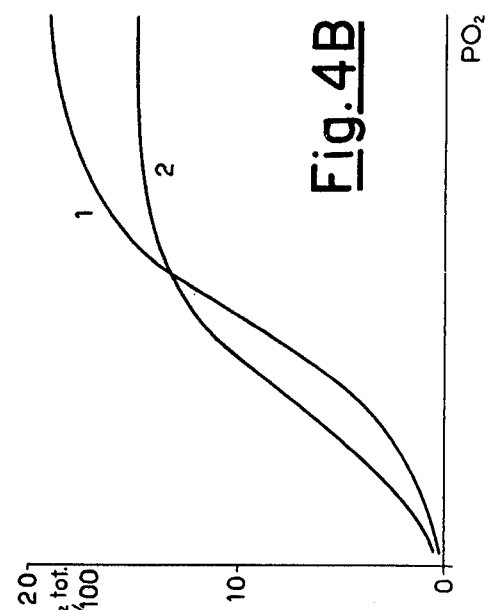
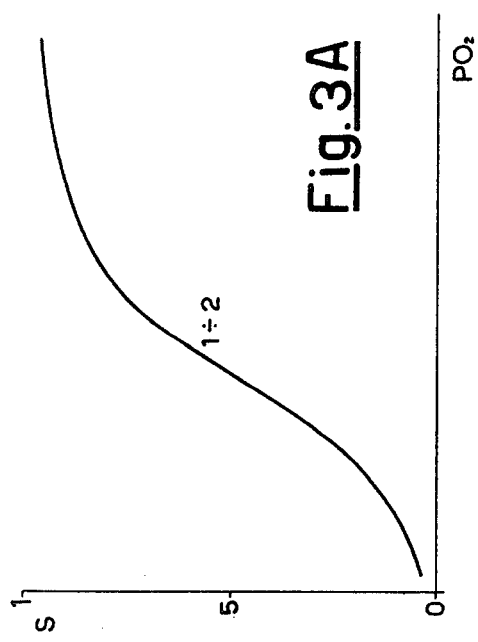
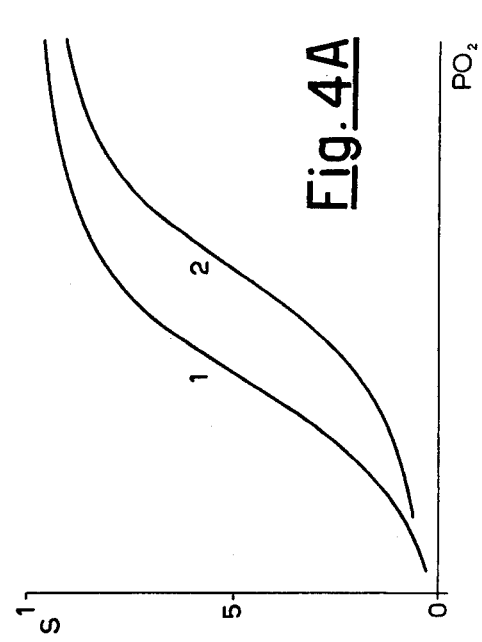

METHOD AND APPARATUS FOR AUTOMATICALLY DETERMINING THE DILUTION CURVE OF A SOLUTION, PARTICULARLY THE OXYGEN DISSOCIATION CURVE OF BLOOD OR HEMOGLOBIN SOLUTIONS

This application is a continuation-in-part of application Ser. No. 598,163, filed July 22, 1975, now abandoned.

Alterations in oxygen affinity and/or oxygen transport properties of blood are best described by changes in the oxygen dissociation curve (ODC). ODC's can be plotted as shown in FIGS. 1A and 1B: 1A — the total oxygen present in blood (e.g., the oxygen chemically combined with hemoglobin plus dissolved oxygen) vs the partial pressure of oxygen ($P_{O_2}$); 1B — the ratio [oxygen chemically bound to the blood/total oxygen combining capacity of blood] vs $P_{O_2}$. Changes in the activity S of small molecules or ions, such as hydrogen-ions, carbon dioxide, 2,3-DPG and/or the presence of abnormal hemoglobins with an altered oxygen affinity, are usually detected by a change in the shape and position of the ODC along its $P_{O_2}$ axis (FIG. 2). Variations in the total hemoglobin concentration of alcool are mainly reflected in the change of its total oxygen capacity (FIG. 3A: S vs $P_{O_2}$ for two blood samples with different oxygen capacity and the same oxygen affinity; FIG. 3B: total $O_2$ vs $f(P_{O_2})$ for the same samples). Other pathological conditions (i.e., carbon monoxide intoxication, formation of methemoglobin, sulfhemoglobin, nitric-oxide hemoglobin, etc.) result in a change both of oxygen capacity and affinity (FIGS. 4A and 4B: S vs $P_{O_2}$ and total $O_2$ vs $f(P_{O_2})$ for two blood samples with different oxygen capacity and oxygen affinity).

The rapid determination of the ODC of whole blood under near physiological conditions of Hb concentration, hematocrit, temperature, pH, $P_{CO_2}$, organic phosphates content, etc. is thus revealing of the alteration of many physiological functions. It is not surprising, therefore, to find that a number of methods have been proposed in the last 100 years or so to experimentally determine the ODC of blood. The classical methods of Barcroft, Van Slyke, Roughton, etc., consist of equilibrating the blood in a tonometer with a gas phase of known $P_{O_2}$. The blood is then sampled and its total oxygen content determined by chemical or spectrophotometric analysis. The oxygen capacity of the sample can be obtained, in a separate experiment, by equilibrating the blood sample with a sufficiently high $P_{O_2}$ to completely (or almost completely) saturate the hemoglobin. This is still the most accurate method available for measuring the ODC of whole blood. However, it is hardly adaptable to routine clinical work.

Many other methods, besides the gasometric one, have been, so far, proposed. Only in a very few cases, however, has proper attention been paid to the careful control of all the factors which are known to affect the ODC. A method whose accuracy approaches the gasometric method has been described by Brenna et al. (Advances in Experimental Medicine and Biology, vol. 28, p. 19-37, 1972, Plenum Press). This method features the adoption of a new tonometric procedure, and of easier spectrophotometric analysis (e.g., by the IL-182 CO-Oxymeter). It allows a substantial saving in the time required to carry on a $P_{50}$ or a complete ODC determination. An identical approach has been more recently proposed by Newman et al. (*Biochemical Medicine*, 8: 72–77, 1973).

All of the methods previously mentioned permit the determination of the ODC only by interpolation through single experimental points. In recent years some methods have been described which can continuously monitor the ODC of whole blood. Franco et al. (*J. Physiol.*, 151: 54P, 1962) described a method which consists of a cuvette containing a suspension of red cells, or whole blood. The $P_{O_2}$ of such a solution is continuously measured by a bare gold electrode using standard polarographic methods. The blood is first equilibrated with a gas phase containing $CO_2$ and enough oxygen to practically saturate the hemoglobin. After the equilibrated blood has been introduced into the cell, the oxygen present in solution (combined plus dissolved) is used up by the addition of a heart-muscle preparation. This method has not been evaluated quantitatively by Franco et al. and no estimation of its accuracy and precision, when applied to the investigation of the functional properties of whole blood, is available. This method requires considerable attention in regard to the handling of the heart-muscle preparation and the aging and poisoning of the $P_{O_2}$ electrode, and thus has not found significant applications in routine clinico-chemistry work. Further modifications of this method, however, have been proposed by Colman and Longmuir (*J. Appl. Physiol.*, 18: 420–423, 1963) and by Longmuir and Chow (*J. Appl. Physiol.*, 28: 343–345, 1970) which attempted to make up for these difficulties. There are many points of criticism to be made of the method on the whole, when applied to the study of the functional properties of blood, one of the most significant being the lack of pH and $P_{CO_2}$ control in solution while the ODC determination is being carried out.

Another example of the "continuous-method" for obtaining the ODC of an erythrocyte suspension has been described by Kiesow et al. (*Clinica Chimica Acta*, 41: 123–139, 1972). The blood here is first diluted ca 300 fold with 0.154 M "bis-tris" buffer, pH = 7.4, with saline, or with a Krebs-Ringer bicarbonate solution, and then completely deoxygenated in a Warburg flask. A few ml of the resulting red cell suspension are then introduced into a special cuvette positioned in a dual-wavelength spectrophotometer and a gradual oxygenation obtained by generating oxygen by the enzymatic decomposition of hydrogen peroxide. The amount of oxyhemoglobin present at any time is obtained from the measured spectral change of the suspension upon oxygenation, and the $P_{O_2}$ from the difference between total oxygen present in solution and the combined oxygen. The method, as described by Kiesow et al. has several drawbacks. The dilution of blood with buffers or other solutions of definite electrolyte content alters the pre-existing conditions of pH and of Donnan equilibrium of the original sample. Such alterations cause a redistribution of electrolytes, such as hydrogen-ions, chloride, etc. across the red cell membrane. In several pathological conditions, the hematocrit, the $P_{CO_2}$, the pH, the mean corpuscular hemoglobin (M.C.H.), and the electrolyte distribution between plasma and red cell is far from normal. The dilution of such pathological samples with saline solutions of normal osmolarity, or with buffers, obviously changes many of their original properties. For example, changes in pH and Hb concentration affect, inter alia, the oxygen affinity of blood by changing the interaction between 2,3-DPG and hemoglobin (Brewer et al., *Advances in Experimental Medicine and*

*Biology*, vol. 28, p. 99, 1972, Plenum Press). It is not surprising, therefore, to find that the $P_{50}$ values determined by Kiesow et al. in their study vary so widely from the accepted values reported in the literature. As an example, Kiesow et al. (FIG. 8, p. 134 of their paper) report, at 37° C, pH = 7.4, a $P_{50}$ of 11.7 mm Hg for erythrocyte suspensions in absence of $CO_2$ with "bis-tris" added. The value determined by Rossi-Bernardi et al. (First Int. Seminar on the Physiological Basis of Anaesthesiology, Milan, May, 1973) on whole blood, under the same experimental conditions of temperature and pH, in absence of "bis-tris" and of $CO_2$, is 24.5. In the presence of ca 35 mm $P_{CO_2}$, Kiesow et al. obtained a $P_{50}$ value of 22.5, against the well known value for human blood of 26 to 27 mm Hg. The $P_{50}$ value reported by Kiesow et al. in absence of $CO_2$ ($P_{50}$ = 26.5) for blood diluted with 0.154 M CaCl is paradoxically higher than that in presence of $CO_2$. $CO_2$ is an allosteric regulator of oxygen affinity which has long been known to shift to the right the ODC of human hemoglobin solutions or whole blood (Kilmartin and Rossi-Bernardi, Physiol. Rev., 53: 836, 1973). Thus, this method, at its present stage of development, does not seem to be able to give meaningful data for physiological or clinico-chemical work.

Another example of a "continuous" method of ODC determination (which has been marketed and sold to the public by the firm Radiometer of Copenhagen, Denmark) is that described by Duvelleroy et al. (*J. Appl. Physiol.*, 28: 227-233, 1970). This method consists in exposing a known volume of blood to a known volume of pure oxygen, in a closed system, and in recording simultaneously the $P_{O_2}$ of the gas and of the liquid phase. The decrease of oxygen in the gas phase, as monitored by one of the $P_{O_2}$ electrodes, is equal to the total oxygen present in solution (oxygen combined plus oxygen dissolved). The main disadvantage of this method (as described by Duvelleroy et al.) lies in the fact that (a) a long time (40 to 50 min) is required to deoxygenate the blood. The deoxygenation is accomplished by a magnetic stirrer which usually causes heavy hemolysis in the sample. A long equilibration time at 37° C produces significant changes in 2,3-DPG or ATP concentration, especially at low pH values. Another disadvantage is that (b) the total sample required is at least ca 7.5 ml; and (c) during the gradual oxygenation the $CO_2$ pressure in the closed system changes. This is due to the well known Bohr effect, according to which reduced blood is more alkaline than oxygenated blood. On the average, 0.083 mM $CO_2$ per mEq oxygen released are taken up by the carbamate reaction of $CO_2$ with hemoglobin. As a result of such changes, (and depending on the volume of the gas phase) the Δ pH between deoxy and oxygenated blood has been found by Duvelleroy et al. to be equal to 0.09. Furthermore, the $P_{CO_2}$ varies from 37 (deoxy) to 43 (oxy) mm Hg. (See for a summary FIG. 3 of Duvelleroy et al.'s paper.) Such changes should increase when the blood is more alkaline than normal (due to a higher carbamate content) or in pathological samples with lower hemoglobin concentration. The resulting ODC curve is thus somewhat distorted from the "physiological" curve which has (i) an average pH shift of ca 0.048 at $P_{CO_2}$ = 40 mm Hg (Rossi-Bernardi and Roughton, J. Physiol., 162: 17-18P, 1962) and (ii) a change of $P_{CO_2}$ in the opposite direction, namely from high $P_{CO_2}$ in the venous to the low $P_{CO_2}$ in the arterial blood. Due to the increased $P_{CO_2}$ of the reduced blood, the "physiological" change in pH undergone by the blood in going from deoxy to oxy and vice versa is indeed somewhat less than the value of 0.048 measured by Rossi-Bernardi and Roughton at constant $P_{CO_2}$. Roughton (Handbook of Respiratory Physiology, USAF School of Aviation Medicine, 1954) estimates that this change should not be greater than 0.03 pH unit when the venous blood becomes oxygenated. The distortion in the ODC, caused by the excessive Δ pH and the inversion of Δ $P_{CO_2}$ described before, as obtained by the Duvelleroy et al. method, can obviously be corrected if a continuous recording of pH and $P_{CO_2}$ is available. Factors for such a correction, however, are approximate and only available for blood under normal conditions of 2,3-DPG, hemoglobin concentration, and in absence of pathological hemoglobins. Even when normal conditions of blood allow the use of such factors, considerable desk work is still needed with this method to recalculate the correct ODC of the original sample in terms of % saturation or to obtain the value of $P_{50}$. Lastly (d), cleaning and bacterial growth control in the measuring cuvette is rather difficult using the instrument in the present configuration.

The preceding discussion has clearly pointed out the main difficulties in obtaining the ODC of whole blood under experimental conditions closely resembling those prevailing in vivo. An invention will now be described which makes it possible to obtain, almost completely automatically, the ODC of whole blood, and more particularly for the determination in the blood of the functions $S = f(P_{O_2})$ and total $O_2 = f'(P_{O_2})$, eliminating most of the practical and theoretical difficulties inherent to other systems.

Figure 6:
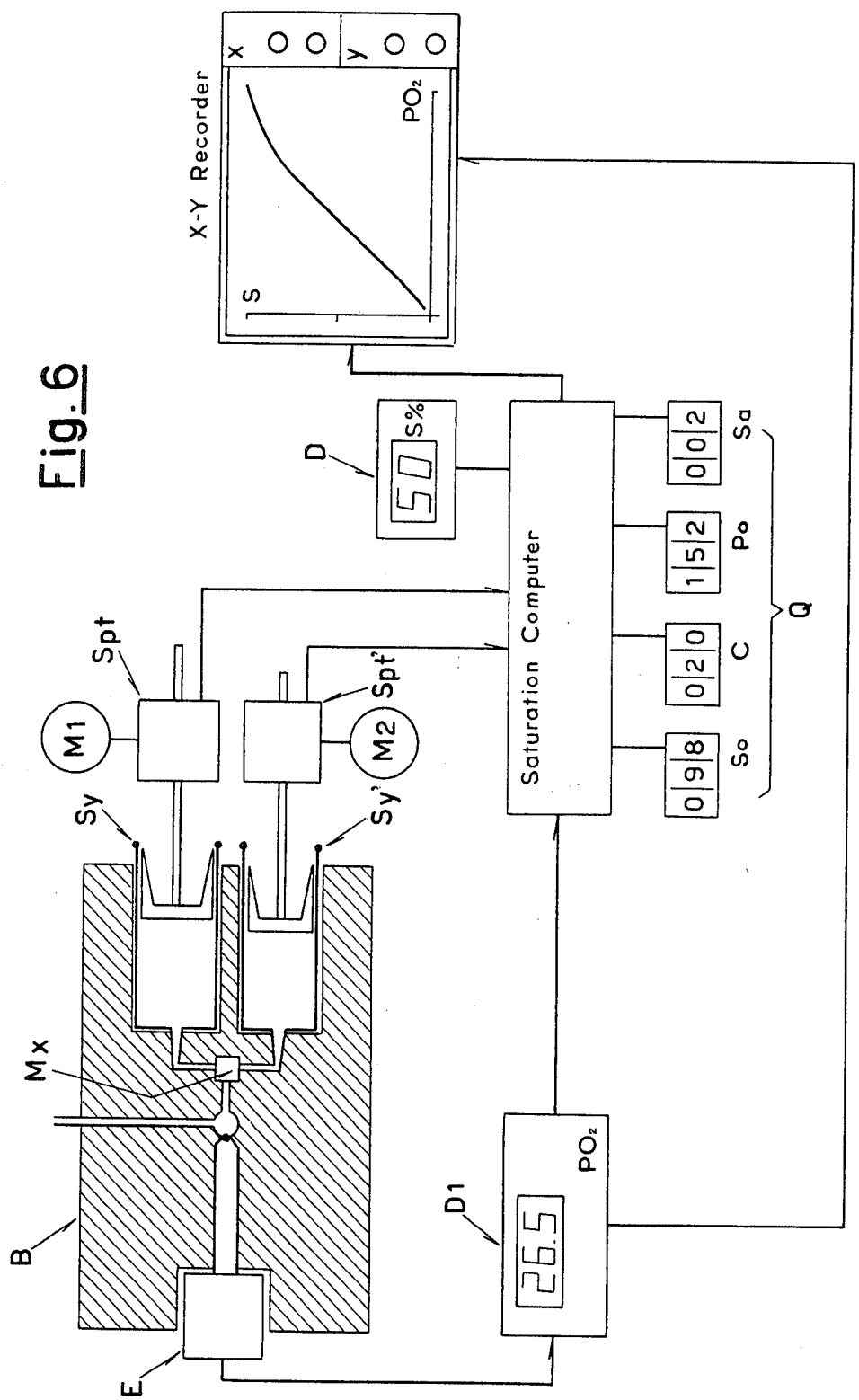

Reference is now made to the drawing in which FIGS. 1A and 1B show oxygen dissociation curves; FIG. 2 changes in ODC which can occur with changes in activity S; FIGS. 3A and 3B show how variations of ODC occur; FIGS. 4A and 4B show changes caused by pathological conditions and FIG. 5 shows a first embodiment of this invention. FIG. 6 shows a schematic diagram of an alternative version of the apparatus described in FIG. 5.

The system is schematically described in FIG. 5. The description is obviously not limitative and is intended mainly to help in the understanding of the functioning of the new method. B is a thermostating block, whose temperature may be controlled either by water circulation or by suitable heating elements, coupled with a thermoregulating device. E is an oxygen electrode, of the Clark type. Sy is a syringe which can be driven at different speeds by $M_1$, a syncronous motor provided with a positional transducer Spt. $V_O$ is the cuvette in which the blood is contained. T is a stopper whose outlet is provided with valve V. Stopper T can move upwards as liquid is fed into $V_O$ by syringe Sy. A stirring button is contained in $V_O$ and is magnetically coupled to motor $M_2$. D and $D_1$ are two digital displays showing the value of S and $P_{O_2}$, S being the percent saturation with oxygen. U is a gas humidifier. The system is completed by an analog computer, whose components are represented in FIG. 5 and will be later discussed in detail, and by an X-Y recorder.

DESCRIPTION OF THE SYSTEM 3 to 4 ml of blood are tonometered in a separate vessel (such as, for example, the IL-237 tonometer) at the required $P_{CO_2}$ (preferably that of the patient), at $P_{O_2}$ = 0. When its oxygen percent saturation has reached ca 4 to 5%, pH and S (if required, see later) are determined (for instance, pH may be determined by a capillary pH electrode and S by a suitable instrument such as the IL-182 CO-Oximeter). The level of 4 to 5% saturation is usually achieved in ca 12 min in the IL-237 tonometer. The blood is sampled from the tonometer into syringe Sy which is then positioned in the thermostating block B. A metal ball or a metal washer can be left in syringe Sy and slowly moved magnetically to prevent sedimentation of the red cells. $M_1$ is activated for a brief period so to discharge 0.5 to 0.8 ml of blood into $V_o$. Stopper T is raised and a suitable gas phase at the same $P_{CO_2}$ as before, but with a $P_{O_2} \sim 200$ to 300 mm, is admitted in $V_o$ from U. $M_2$ is activated and the blood in $V_o$ is equilibrated with the gas phase, until its $P_{O_2}$ reaches 100 to 110 mm. At this point a small amount of blood from $V_o$ is sampled (for instance, through an IL-182 CO-Oximeter) and its $S_o$, total Hb and % HbCO determined. The blood pH may also be measured by a capillary pH electrode. It should be added, if one wishes to use the CO-Oximeter that, neglecting any methemoglobin, which is usually very low in blood, the oxygen capacity of the sample in $V_o$ is given by total Hb - (total Hb) × % HbCO.

Stopper T is now lowered to a preset stop and valve V is closed. The all liquid system in $V_o$ has a known, calibrated volume. The small bore tubing from $V_o$ to valve V contains ca 10 to 15 μl of blood which does not partecipate in the subsequent reaction. The known values of $S_o$, C, $P_o$ ($P_o$ is the oxygen partial pressure of the sample present in $V_o$, as measured by the $P_{O_2}$ electrode) are then introduced into the computing system through the four digital switches Q Motor $M_1$ is then switched on, pushing the deoxy blood contained in syringe Sy, at a constant speed, into the oxy blood contained in $V_o$. By knowing the speed of the syringe and P, the oxygen pressure in $V_o$ at any given time, the % saturation of the mixture in $V_o$ can be calculated at any time, and plotted in the X/Y recorder against the $P_{O_2}$ given by the $P_{O_2}$ electrode. If a reasonably fast $P_{O_2}$ electrode is used, a complete oxygen dissociation curve can be recorded in ca 15 min. The complete procedure (starting from a sample of blood to a complete ODC determination) does not require longer than 30 min. The percent saturation S in the mixture can quantitatively be obtained from the following considerations.

The total oxygen present in the volume of blood $V_o$ (in ml or moles) equals initially:

$$\text{Total } O_2(V_o) = V_o(S_oC + \alpha P_o) \qquad [1]$$

where $V_o$ = initial volume, $S_o$ = initial % saturation, C = oxygen capacity, $\alpha$ = coefficient of oxygen solubility in blood, and $P_o$ = the oxygen partial pressure of the oxygenated sample in $V_o$.

At any given time $t$, syringe Sy has discharged into $V_o$ a blood volume = $V_a$ = Kt, K being the flow rate of discharge of Sy into $V_o$. The total oxygen contained in the volume $V_a$ of blood equals $$\text{Total } O_2(V_a) = V_a(S_aC + \alpha P_a) \qquad [2]$$

where $V_a$ = volume of blood discharged from the syringe after time $t$, $S_a$ = % oxygen saturation of blood contained in the syringe, $\alpha$ = coefficient of oxygen solubility in blood, and $P_a$ = the oxygen partial pressure of the deoxygenated sample in the syringe.

The total oxygen in the mixed liquid is obviously the sum of eqs. [1] and [2], i.e., $$\text{Total } O_2(V_m) = (V_o+V_a)(S \times C + \alpha P) = V_o(S_oC + \alpha P_o) + V_a(S_aC + \alpha P_a) \qquad [3]$$

whence $$S = \frac{V_o(S_oC + \alpha P_o) + V_a(S_aC + \alpha P_a) - \alpha(V_o + V_a)P}{(V_o + V_a)C} \qquad [4]$$

The term $\alpha P_a$, if $P_a$ is less than 4 to 5 mm Hg, may be neglected in comparison with the other terms of eq. [4].

$$S\% = \frac{V_oS_o + V_aS_a}{V_o + V_a} + \frac{\alpha P_oV_o}{(V_o + V_a)C} - \frac{\alpha P}{C} \qquad [5]$$

If we can assume that the oxygen content in syringe Sy is close to zero (a condition that can be obtained at the cost of longer equilibrating times in the tonometer), then eq. [5] reduces to $$S = \frac{V_oS_oC + \alpha V_oP_o - \alpha(V_o + V_a)P}{(V_o + V_a)C} \qquad [6]$$

The analog computer represented in FIG. 5 has been typically designed to solve eq. (5) from known values of $V_O$ and $\alpha$. More particularly in the scheme of FIG. 5, Qo is a digital switch, of a type per se known, comprising internal resistances which are set to correspond to the saturation value $S_o(\%)$ of the oxygenated blood; Qa is a digital switch, like Qo, which is set with a value corresponding to the saturation $S_e(\%)$ of the deoxygenated blood; Q (Po) is a third digital switch, set with a value corresponding to the oxygen partial pressure Po (mm Hg) of the oxygenated blood; Q (C) and Q (C') on digital switches, in which values corresponding to the capacity C (ml $O_2$ per 100 mls of blood) of the blood under analysis (Q (C) and Q (C') being coupled under only one control); Vo, Vo' and Vo", are constant resistances the value of which is proportional to the volume of the measuring cuvette; Va and Va' are variable resistances, coupled to the syringe Sy, having a value proportional to the volume of blood emitted by Sy (Va and Va' being coupled under only one control); alpha is a constant resistance proportional to the solubility coefficient of the oxygen into the blood; V$\alpha$ is a voltage proportional to the said solubility coefficient of the oxygen into the blood; R and R' are resistances of a value selected so as to have the voltage value at the output of the amplifier $A_5$ (later described) numerically coincident with the saturation value (%); $A_1$ and $A_2$ are operational amplifiers, per se known, by which the ratio (Vo So + Va Sa)/ (Vo + Va) are calculated; $A_3$ is an operational amplifier by which the ratio $\alpha$ PoVo / (Vo + Va)C is calculated; $A_4$ is an operational amplifier by which the ratio $\alpha$ P/C is calculated; $A_5$ is an operational amplifier by which the value $$S\% = \frac{VoSoC + VaSaC + \text{alpha } PoVo - \text{alpha}P(Vo + Va)}{(Vo + Va)C}$$

is calculated; D and $D_1$ are digital display devices, showing the numerical values of S (%) and of the measures carried out by the electrode E, and X Y is a potentiometric plotting recorder reporting the function $V_s = f(V_P)$. Experimentally determined values of $S_o$, C, $P_o$ and $S_a$ can be introduced into the computer through the respective digital switches $Q_O$, $Q_a$, $Q_{P_O}$ and $Q_{Q(c)}$, $Q_{(c')}$ shown in FIG. 5. The principles on which the analog computer operates for solving eq. (5) are as follows: Spt (FIG. 5) is a positional transducer which operates on the dual gang potentiometer $V_a$ so that the position of the piston of syringe Sy (and thus the volume of solution introduced in cuvette C) is fed into the analog computer. Amplifiers $A_1$ and $A_2$ give an electrical putput proportional to $[V_oS_o + V_aS_a] / [V_o + V_a]$. The electrical circuit associated with amplifier $A_3$ gives an output p proportional to $P_oV_o / [(V_o + V_a) C]$ whereas $A_4$ and associated components will give an output proportional to aP/C. Amplifier $A_5$ sums the output of $(A_1 + A_2)$, $A_3$ and $A_4$ solving eq. (5). The value of S can be read on the digital voltmeter D and/or plotted versus $P_{O_2}$ by the X-Y recorder.

Eq. (5) clearly shows that only at time = oo does S = O, a condition which, obviously, is not attainable experimentally. Thus, the method described is practically limited in the exploration of the lower bottom of the ODC by the size of $V_o$ and $V_a$ relative to each other. Practical reasons (e.g., the size of the $P_{O_2}$ electrode) restrict $V_o$ to the range of 0.2 ml < $V_o$ < 0.5 ml and $V_a$ to 0.2 < $V_a$ < 5 ml. The range of S which can experimentally be obtained is thus approximately 0.04 < S < 1. This range is more than sufficient, however, for a meaningful study of the functional properties of blood, either for physiological or clinical work. Obviously, if one wishes to study the ODC starting from the lower end, it is only necessary to start with deoxygenated blood in $V_o$ and oxygenated blood in syringe Sy.

FIG. 6 shows a schematic diagram of an alternative version of the apparatus described in FIG. 5. Sy and Sy' are two syringes respectively containing oxygenated (at a given $P_{CO_2}$) and deoxygenated blood (at the same or at another convenient $P_{CO_2}$). B is a thermostating block, whoe temperature may be controlled either by water circulation or by suitable heating elements, coupled with a thermoregulating device. E is an oxygen electrode, Mx is a mixing chamber. M1 and M2 are two motors to drive the two syringes. D and D1 are two digital electronic display. Q represents a set of digital switches to set initial values of So, C, Po and Sa.

DISCUSSION

In the preceding pages a new invention has been discussed. The invention permits the determination of the ODC of whole blood under near physiological conditions of pH, hemoglobin concentration, $P_{CO_2}$, organic phosphates concentration, etc. The new invention is based on (a) the principle of continuously mixing oxygenated and deoxygenated blood, (b) the continuous measurement of $P_{O_2}$ by the oxygen electrode, and (c) the computation, in line with the mixing, of the function S = $f(P_{O_2})$ by an analog computer. The principle of mixing oxy- and deoxygenated blood to obtain single points on the ODC of whole blood is not new (Haab et al., J. Appl. Physiol., 15: 1148-1149, 1960; Edwards and Martin, J. Appl. Physiol., 21: 1898-1902, 1966). The new principles (a) to (c) introduced in this patent now make possible the automatic recording of the ODC of whole blood on a continuous basis. This method differs from the previously described methods (see Introduction) to obtain ODC, in allowing strict adherence of the ODC so determined to the physiological and pathological conditions met in vivo. Thus, by varying to an appropriate extent the $P_{CO_2}$ of the oxy- and deoxygenated samples of blood, an ODC closely simulating the ODC of a single patient can be obtained.

I claim:

1. A method for automatically determining the oxygen dissociation curve of whole blood or of hemoglobin solution, comprising the steps of continuously admixing a first sample of blood or hemoglobin solution containing oxygen at a known predetermined saturation level with a second sample of blood or hemoglobin solution at a different saturation level, continuously measuring the oxygen dissolved in the mixture, converting said measurement into an electrical signal, comparing said signal with reference values related to the said blood or hemoglobin solution having the predetermined saturation level, measuring the partial pressure of oxygen dissolved in the mixture and calculating the functions S = f ($P_o$) and Total O = f' ($P_o$) according to the equations:

$$S = \frac{V_oS_oC - a V_oP_o - a(V_o + V_a) P}{(V_o + V_a) C} \text{ and}$$

$$\text{Total } O = \frac{V_o(S_oC + oP_o) + V_a(S_aC + a P_a)}{}$$

in which:
  $V_o$ is the known volume of solution having said predetermined saturation level of oxygen,
  $S_o$ is the value of S calculated for the volume $V_o$,
  C is the capacity of the solvent towards oxygen,
  a is the solubility coefficient of blood or hemoglobin solutions,
  $P_o$ is the partial pressure of oxygen in the known volume $V_o$,
  $V_a$ is the volume of the sample added and mixed with $V_o$ at a time t,
  P is the partial pressure of oxygen in the mixture at the time t,
  $S_a$ is the value of S for the mixture at the time t, the calculation being carried out in real time with respect to the mixing,
and
  determining said dilution curve from the calculations.

2. A method according to claim 1, wherein the first sample is a sample of blood saturated with oxygen up to a predetermined level and the second sample is deoxygenated blood.

3. A method according to claim 2, wherein said step of admixing includes admixing the second sample of deoxygenated blood gradually with the entire first sample of oxygen saturated blood.

4. A method according to claim 3, wherein said step of determining includes plotting the values calculated by the computer on an X/Y recorder, whereby at the end of the mixing of the two samples, the oxygen dissociation curve of the blood under testing is obtained.

5. A method according to claim 4, wherein the step of plotting includes programming the display means of the recorder to hold the value of the oxygen partial pressure when S = 50 whereby the value of $P_{50}$ of the sample under analysis is automatically obtained.

6. A method according to claim 2, wherein said step of admixing includes mixing the two samples of blood, respectively saturated and deoxygenated, simultaneously at predetermined flow rates, and the oxygen partial pressure is measured on the mixture, as it is at a given time t.

7. An apparatus for automatically determining the oxygen dissociation curve of the whole blood or of hemoglobin solutions, comprising:
a thermostated mixing and measuring chamber,
first dosing means for feeding to the said chamber blood saturated with oxygen at a predetermined level;
second dosing means for feeding to the said chamber deoxygenated blood; means for measuring the partial pressure of the oxygen on the mixture which is formed in said chamber and converting the measurement into an electrical signal; an analogic computer, for receiving said signal and containing basic or reference data related to the oxygenated blood for calculating, in real time with respect to the mixing, the functions $S = f(P_{O_2})$ and Total $O_2 = f'(P_{O_2})$, and recording means for recording the calculated values of the two above said functions.

8. An apparatus according to claim 7, wherein said measuring means is an oxygen electrode.

9. An apparatus according to claim 7, wherein said first dosing means and said second dosing means are coincident, whereby said deoxygenated blood is fed to said chamber only after all the sample of oxygenated blood has been fed to the said chamber.